US006488946B1

(12) United States Patent
Milius et al.

(10) Patent No.: US 6,488,946 B1
(45) Date of Patent: Dec. 3, 2002

(54) STABLE WATER-IN-OIL EMULSIONS CONTAINING AN EMULSIFIER ON OLEYL-AND/OR ISOSTEARYL-GLYCOSIDE

(75) Inventors: Alain Milius, Nice (FR); Alicia Roso, Saix (FR); Nelly Michel, Maisons Alfort (FR)

(73) Assignee: Societe d'Exploitation de Produits pour les Industries Chimiques-S.E.P.P.I.C., Paris Cedex (FR)

( * ) Notice: Subject to any disclaimer, the term of this patent is extended or adjusted under 35 U.S.C. 154(b) by 0 days.

(21) Appl. No.: 09/936,695
(22) PCT Filed: Mar. 17, 2000
(86) PCT No.: PCT/FR00/00656
§ 371 (c)(1),
(2), (4) Date: Sep. 17, 2001
(87) PCT Pub. No.: WO00/56438
PCT Pub. Date: Sep. 28, 2000

(30) Foreign Application Priority Data

Mar. 19, 1999 (FR) .............................. 99 03429

(51) Int. Cl.$^7$ ........................ A61K 7/00; A61K 31/045; C07G 3/00
(52) U.S. Cl. ........................ 424/401; 424/400; 514/724; 514/937; 514/938; 514/939; 536/4.1; 536/18.6
(58) Field of Search ................................ 424/400, 401; 514/724, 937, 938, 939; 536/4.1, 18.6

(56) References Cited

FOREIGN PATENT DOCUMENTS

WO          98 22207          5/1998

*Primary Examiner*—Shelley A. Dodson
(74) *Attorney, Agent, or Firm*—Dennison, Schultz & Dougherty

(57) ABSTRACT

The present invention relates to novel stable <<water-in-oil>> emulsions containing 5 to 70% by weight of an aqueous phase
20 to 90% by weight of a fatty phase; and
3 to 25% by weight of an emulsifier comprising
  10 to 90% by weight, preferably 10 to 50% by weight and more preferably 10 to 40% by weight of a mixture in any proportion of an oleyl glycoside having a degree of polymerisation of between 1 and 3 and an isostearyl glycoside having a degree of polymerisation of between 1 and 3; and
  90 to 10% by weight, preferably 90 to 50% by weight, and more preferably 90 to 60% by weight of a mixture in any proportion of oleyl alcohol and isostearyl alcohol and optionally 0 to 10% by weight of a co-emulsifier;
0 to 10% by weight of a stabiliser.

Application: Cosmetic industry.

32 Claims, No Drawings

STABLE WATER-IN-OIL EMULSIONS CONTAINING AN EMULSIFIER ON OLEYL-AND/OR ISOSTEARYL-GLYCOSIDE

BACKGROUND OF THE INVENTION

Novel stable water-in-oil emulsions containing an oleyl glycoside-based and/or isostearyl glycoside-based emulsifier.

An object of the present invention is novel stable water-in-oil emulsions containing an oleyl glycoside-based and/or isostearyl glycoside-based emulsifier.

The invention especially finds application in the cosmetic field.

Alkyl glycosides or alkyl polyglycosides (APG's) are well-known non-ionic surfactant compounds which can be used alone or in combination with other surfactants in a wide range of industrial applications, and especially in the cosmetic field.

Alkyl polyglycosides have firstly been used as foaming agents, and in this application, those the alkyl chain of which comprises 8 to 14 carbon atoms have proved to be particularly interesting.

More recently, alkyl polyglycosides have been used as emulsifiers, and in this application, those the alkyl chain of which comprises 16 to 18 carbon atoms have proved to be particularly interesting.

The patent application WO 92/06778, in the name of the Applicant, describes, for the first time, the use of mixtures of alkyl polyglycosides and fatty alcohols as self-emulsifying agents.

The term <<self-emulsifying>> designates any agent or composition which is capable of forming a stable emulsion with an aqueous phase, practically without the provision of energy, for example by dispersion in the aqueous phase by slow mechanical agitation.

More specifically, the mixtures described in this prior art document comprise:

60 to 90% by weight of at least one fatty alcohol having 12 to 22 carbon atoms, and preferably 16 to 18 carbon atoms; and 10 to 40% by weight of an alkyl polyglycoside, the alkyl part of which is preferably identical to that of the fatty alcohol.

The self-emulsifiable compositions described in the above-mentioned application are marketed under the designation Montanov® 68 and comprise a mixture of alkyl polyglycosides the fatty chains of which comprise 16 and 18 carbon atoms, as well as a mixture of fatty alcohols of the same fatty chain length.

In Example 3.5 of this prior art document, an emulsion is described which contains:

5% by weight of a fatty phase constituted of cetyl stearyl octanoate,

10% by weight of a self-emulsifying composition based on oleyl glycoside and oleyl alcohol.

This emulsion is of the classic oil-in-water type.

After the WO 92/06778 patent application, numerous patent documents have described the use of emulsifying or self-emulsifying compositions based on alkyl polyglycosides and fatty acids for the preparation of emulsions.

It is envisaged in these documents to use alkyl glycosides of various nature, the alkyl part of which can be branched and/or unsaturated, and present 4 to 54 carbon atoms.

If some of these documents also explicitly envisage the use of oleyl glycoside or isostearyl glycoside, such as the documents WO 97/02091 or WO 97/18033 for example, it is always under conditions which lead to the preparation of classic oil-in-water emulsions.

Consequently, none of these prior patents specifically cover the preparation of water-in-oil emulsions which are however of considerable interest, especially in the cosmetic field.

SUMMARY OF THE INVENTION

It has been discovered, and this constitutes the basis of the present invention, that oleyl glycoside-based and/or isostearyl glycoside-based emulsions combined with mixtures of oleyl alcohol and isostearyl alcohol can be used, under certain conditions, as emulsifiers for preparing water-in-oil emulsions.

This discovery is entirely unexpected, insofar as it has been furthermore noticed that compositions based on alkyl glycosides and corresponding fatty acids, such as an isooctadecyl glycoside for example, or an alkyl glycoside obtained from a Guerbet alcohol having 18 carbon atoms do not enable water-in-oil emulsions to be obtained.

DETAILED DESCRIPTION OF THE INVENTION

Thus, according to a first aspect, the object of the present invention is novel stable <<water-in-oil>> emulsions, containing:

5 to 75% by weight of an aqueous phase;

20 to 90% by weight of a fatty phase; and 3 to 25% by weight of an emulsifier comprising:

10 to 90% by weight, preferably 10 to 50% by weight and more preferably 10 to 40% by weight of a mixture in any proportion of an oleyl glycoside having a degree of polymerisation of between 1 and 3 and an isostearyl glycoside having a degree of polymerisation of between 1 and 3; and 90 to 10% by weight, preferably 90 to 50% by weight, and more preferably 90 to 60% by weight of a mixture in any proportion of oleyl alcohol and isostearyl alcohol and optionally:

0 to 10% by weight of a co-emulsifier;

0 to 10% by weight of a stabiliser.

Advantageously, the novel water-in-oil emulsions in accordance with the present invention contain 10 to 70% by weight of an aqueous phase 25 to 60% by weight of a fatty phase; and 5 to 15% by weight of an emulsifier comprising 10 to 90% by weight, preferably 10 to 50% by weight and more preferably 10 to 40% by weight of a mixture in any proportion of an oleyl glycoside having a degree of polymerisation of between 1 and 3 and an isostearyl glycoside having a degree of polymerisation of between 1 and 3; and 90 to 10% by weight, preferably 90 to 50% by weight, and more preferably 90 to 60% by weight of a mixture in any proportion of oleyl alcohol and isostearyl alcohol and optionally:

0 to 10% by weight of a co-emulsifier;

0 to 5% by weight of a stabiliser.

Stable water-in-oil emulsions which are particularly preferred within the context of the present invention contain:

10 to 25% by weight of an isostearyl glycoside having a degree of polymerisation of between 1 and 3; and 90 to 75% by weight of an isostearyl alcohol.

Within the context of the present description, the expressions "oleyl glycoside having a degree of polymerisation of between 1 and 3" and "isostearyl glycoside having a degree of polymerisation of between 1 and 3", are understood as meaning compounds of formula:

$$RO(G)_x$$

in which:

R represents an oleyl and isostearyl radical, respectively, and x represents a number between 1 and 3;

G represents a reducing glycopyranose or glycofuranose residue and preferably a glucose residue.

Advantageously, the degree of polymerisation of these alkyl glycosides represented by x is of between 1.05 and 2.5; and more preferably, between 1.1 and 2.

The alkyl glycosides used within the context of the present invention as emulsifiers are compounds the alkyl radicals of which are defined as indicated above.

However, these compounds are not always pure.

They can in fact further contain minor proportions of compounds of the same nature the alkyl radicals of which comprise a longer and/or shorter chain, such compounds originating especially from fatty acids generally of natural or synthetic origin which are used as starting material for the synthesis of these compounds.

The term <<minor proportion>> is understood as meaning a maximum combined amount of 5% by weight, and preferably of 1% by weight with respect to the total weight of the alkyl glycosides mentioned above.

The compositions based on isostearyl glycoside and isostearyl alcohol have proved to be particularly interesting as an emulsifier for preparing stable water-in-oil emulsions.

The expression <<mixture in any proportion>> is thus understood to cover the use of oleyl glycoside or isostearyl glycoside alone, i.e. mixtures are made which comprise 0 to 100% by weight of both of the constituents mentioned above.

The compositions based on oleyl glycoside and/or isostearyl glycoside and oleyl alcohol and/or isostearyl alcohol used as an emulsifier within the context of the present invention can be prepared by simply mixing their constituents in the pre-determined proportions sought after.

On an industrial scale, they will be prepared preferably according to one of the two routes classically used for the synthesis of alkyl polyglycosides, and notably by reaction, in an acid medium, between the corresponding fatty alcohol (s), and a saccharide having an anomeric OH group, such as glucose or dextrose.

Such synthetic routes are well known and have been widely described in the literature and in particular in the documents cited in the introduction.

If need be, it will be possible for this synthesis to be completed by operations of neutralisation, filtration, distillation or partial extraction of the excess fatty alcohol, or of discoloration.

In general, the novel emulsions in accordance with the present invention contain 20 to 90% by weight, preferably 20 to 60% by weight of a fatty or oily phase.

This fatty phase can be constituted by one or more oils selected from the following oils oils of plant origin, such as sweet almond oil, coconut oil, castor oil, jojoba oil, olive oil, rapeseed oil, groundnut oil, sunflower oil, wheat germ oil, maize germ oil, soya oil, cotton oil, lucerne oil, poppy oil, marrow oil, evening primrose oil, millet oil, barley oil, rye oil, safflower oil, canelle nut tree oil, passionflower oil, hazelnut oil, palm oil, shea butter, apricot stone oil, Alexandria laurel tree oil, sysymbrium oil, avocado oil, calendula oil;

modified plant oils such as the products known under INCI designations Apricot Kernel Oil PEG-6 esters and Olive Oil PEG-6 esters;

oils of natural origin, such as perhydrosqualene, squalene;

mineral oils, such as liquid paraffin, and mineral oils, notably originating from petroleum fractions, such as isoparaffins, having a boiling point between 300 and 400° C.;

synthetic oils, notably fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, ester derivatives of lanolic acid, such as isopropyl lanolate, isocetyl lanolate, monoglycerides, triglycerides such as glycerol triheptanoate, alkylbenzoates, isoparaffins, polyalphaolefins, polyolefins, such as polyisobutylene, synthetic isoalkanes such as isohexadecane, isododecane, perfluorinated oils, and silicone oils. Amongst the latter oils, dimethyl polysiloxanes, methylphenylpolysi loxanes, amine-modified silicones, fatty acid-modified silicones, alcohol-modified silicones, alcohol- and fatty acid-modified silicones, polyether group-modified silicones, epoxy-modified silicones, fluoro group-modified silicones, cyclic silicones, and alkyl group-modified silicones, may be more particularly cited.

This fatty phase can also contain one or more compounds selected from the fatty acids, fatty alcohols, waxes of natural or synthetic origin, and even more generally any fatty body of plant, animal or synthetic origin.

In general, the emulsions in accordance with the present invention contain 5 to 70% by weight, preferably 10 to 70% by weight, of a hydrophilic phase which is essentially constituted of water and optionally a hydrophilic solvent, such as glycerine for example.

The emulsions in accordance with the present invention can also contain, optionally, up to 100% by weight of a co-emulsifier and up to 100% by weight of a stabiliser.

Amongst the co-emulsifying agents which can be used within the context of the present invention, mention will be made especially of lipoamino acids and their salts, lipopeptides and their salts, non-ionic and anionic silicone emulsifiers, esters of sorbitan, esters of polyglycerol, hydrogenated ethoxylated castor oil, glycerol stearate, polyglycol polyhydroxystearates such as the product designated as HYPERMER® for example, ethoxylated plant oils, methyl esters of ethoxylated plant oils, ethoxylated sorbitan esters such as the products marketed under the designation POLYSORBATE 81®, POLYSORBATE 61® and POLYSORBATE 21® for example; acylates of proteins which are weakly ethoxylated (with 1 to 3 EO groups); cationic emulsifiers such as aminoxides, quaternium 82 and surfactants described in patent application WO 96/00719 and mainly those the fatty chain of which comprises at least 16 carbon atoms; sucrose esters, ethoxylated or non-ethoxylated methyl glucoside esters; ethoxylated fatty acids; ethoxylated fatty alcohols; anionic emulsifiers such as decyl phosphate or cetearyl sulphate.

Advantageously, a sorbitan ester, particularly such as a sorbitan oleate in particular will be used within the context of the present invention as co-emulsifier.

Amongst the stabilising agents which can be used within the context of the present invention, mention may be made of hydrogenated castor oil, plant waxes such as, for example, beeswax and carnauba wax, stearic acid, aluminium polyoxystearate, such as, for example, the product marketed under the designation MANALOX®, magnesium stearate, aluminium stearate, hydrophobic silicas, polyethylene glycol-alkyl glycol copolymers, polymers such as the products marketed under the designation KRATON® by the company SHELL CHEMICALS, mineral waxes such as ozokerite.

Advantageously, the stabilising agent will be a polyethylene glycol-dodecyl glycol copolymer, notably PEG-45 dodecyl glycol copolymer, such as the product marketed under the designation ELFACOS ST 9 ®, by the company AKZO NOBEL.

In a particularly preferred embodiment, use will be made as co-emulsifier and stabiliser of a mixture of beeswax, hydrogenated castor oil, stearic acid and sorbitan oleate, particularly such as the product marketed under the designation MONTANE® 481, by the company SEPPIC.

It will be possible for the stable water-in-oil emulsions in accordance with the invention to be prepared by simple dispersion, at a temperature of between 15° C. and 85° C., of the aqueous phase in the fatty phase, in the presence of the emulsifier, and optionally of the co-emulsifier and/or of the stabiliser, these latter compounds being generally present within the fatty phase.

In a way known per se, these emulsions can further comprise one or more compounds selected from moisteners, such as, for example, glycerine, preservatives, such as, for example, the products known under the designation SEPICIDE®, colorants, perfumes, cosmetic active principles, mineral or organic solar filters, mineral fillers such as iron oxides, titanium oxides and talc, synthetic fillers such as nylons and micropearls and plant extracts.

It will be possible for these compounds to be introduced into the aqueous phase or into the fatty phase, according to their affinity for these phases, be it during the dispersion phase mentioned above, or in relation to compounds which are sensitive to temperature, afterwards during the cooling phase in the case in which the dispersion is carried out in the hot.

According to a second aspect, the object of the present invention is the use of a composition comprising:

10 to 90% by weight, preferably 10 to 50% by weight and more preferably 10 to 40% by weight of a mixture in any proportion of an oleyl glycoside having a degree of polymerisation of between 1 and 3 and an isostearyl glycoside having a degree of polymerisation of between 1 and 3; and 90 to 10% by weight, preferably 90 to 50% by weight, and more preferably 90 to 60% by weight of a mixture in any proportion of oleyl alcohol and isostearyl alcohol as an emulsifier intended for the preparation of a stable water-in-oil emulsion.

The invention will be illustrated in greater detail by the following Examples, which are given as an illustration only.

EXAMPLE 1

Method of Preparation of a Composition Based on Isostearyl Glycoside and Isostearyl Alcohol, which is Useful as an Emulsifier for Preparing a Water-in-oil Emulsion According to the Invention Isostearyl alcohol (product marketed by the company UNICHEMA under the designation PRISORINE® 3515, or by the company HENKEL under the designation SPEZIOL C18 ISO) is introduced into a polyvalent reactor.

Glucose is also introduced into the reactor, such that the molar ratio between the isostearyl alcohol and the glucose be: 6/1.

Then, the glucose is allowed to react with the fatty alcohol over 6 hours at a temperature of about 100° C., in the presence of an acidic catalyst under partial vacuum.

After reaction, the catalyst is neutralised by means of a base.

The composition obtained has the following analytic features:

aspect: liquid.

EXAMPLE 2

Method of Preparation of a Composition Based on Oleyl Glycoside and Oleyl Alcohol, which is Useful as an Emulsifier for Preparing a Water-in-oil Emulsion According to the Invention The composition of Example 2 was made by following the experimental method described in Example 1, but by replacing isostearyl alcohol by oleyl alcohol.

The analytic features of the product thus obtained are the following:

aspect: liquid.

COMPARATIVE EXAMPLES 1 to 6

Various emulsifiers were prepared which are based on alkyl polyglycosides and fatty acids in order to demonstrate the particular properties of the mixtures based on oleyl glycoside and/or isostearyl glycoside used within the context of the present invention.

The product of Comparative Example 1 was prepared by following the experimental method of Example 1, so as to obtain a composition based on cetearyl glycoside and cetearyl alcohol as defined in Examples R3 and R4 of the document WO 97/18033.

The product of Comparative Example 2 was prepared by following the experimental protocol described in Example 1 of the document WO 92/06778.

The product of Comparative Example 3 was prepared by following the experimental protocol of Example 4 of the document WO 97/02091.

The product of Comparative Example 4 was prepared by following the experimental method of Comparative Example F of the document WO 98/22207.

The product of Comparative Example 5 was prepared by following the experimental protocol described in Example 1 and by replacing isostearyl alcohol by isooctadecyl alcohol (C18 oxo alcohol marketed by the company HOECHST).

The analytic features of the product thus obtained are the following:

aspect: liquid.

The product of Comparative Example 6 was prepared by following the experimental method of Example 1 by replacing isostearyl alcohol by a C18 Guerbet alcohol, marketed by the company Comdea under the designation ISOFOL® 18T.

The analytic features of the product thus obtained are the following:

aspect: liquid.

The various qualitative and quantitative compositions of the products of Examples 1 and 2 and of the Comparative Examples 1 to 6 are grouped in Table 1 below.

TABLE I

| Composition: | Ex 1 | Ex 2 | Comp 1 | Comp 2 | Comp 3 | Comp 4 | Comp 5 | Comp 6 |
|---|---|---|---|---|---|---|---|---|
| Free fatty alcohols | | | | | | | | |
| $C_{12}$ | | | | | 0.3% | 8.0% | | |
| $C_{14}$ | | | | | 1.4% | 15.3% | | |
| $C_{16}$ | | | 25.0% | 43.9% | 4.9% | 10.1% | | |
| $C_{18}$ | | | 25.0% | 43.9% | 9.7% | 12.4% | | |
| oleyl | | 81.9% | | | 22.7% | 27.4% | | |
| isostearyl | 83.9% | | | | | | | |
| isooctadecyl | | | | | | | 94.0% | |
| Guerbet C18 | | | | | | | | 94.5% |
| Total | 83.9% | 81.9% | 50.0% | 87.8% | 39.0% | 73.2% | 94.0% | 94.5% |
| APG | | | | | | | | |
| $C_{12}$ | | | | | 5.4% | 2.4% | | |
| $C_{14}$ | | | | | 11.0% | 4.8% | | |
| $C_{16}$ | | | 25.0% | 6.1% | 9.8% | 4.3% | | |
| $C_{18}$ | | | 25.0% | 6.1% | 9.8% | 4.3% | | |
| oleyl | | 18.1% | | | 25.0% | 11.0% | | |
| isostearyl | 16.1% | | | | | | | |
| isooctadecyl | | | | | | | 6.0% | |
| Guerbet C18 | | | | | | | | 5.5% |
| total | 0.0% | 18.1% | 50.0% | 12.2% | 61.0% | 26.8% | 6.0% | 5.5% |

EXAMPLE 3

Demonstration of the Remarkable Properties of the Compositions Based on Oleyl Glycoside and/or Isostearyl Glycoside as an Emulsifier for Preparina Stable Water-in-oil Emulsions Emulsion were prepared by using the products of Examples 1 and 2 and of Comparative Examples 1 to 6 as emulsifier under the conditions described in the state of the art, and in particular in Example 3 of the document WO 92/06778.

Under the experimental conditions used, (up to 17% by weight of fatty phase and 5% by weight of emulsifier), all the products of the Examples as well as the Comparative Examples led to obtaining classic oil-in-water emulsions (determination by the drop method).

Novel emulsions were then prepared by using a fatty phase based on paraffin oil in an amount by weight of y %, the emulsifier being used in an amount of x % by weight.

The emulsions thus prepared have the following compositions emulsifying system: x % stabiliser (PEG 45 dodecyl glycol copolymer=ELFACOS ST 9 from AKZO):2% fatty phase: y %

MgSO4: 0.7% glycerine: 5% preservative: qsp water: qsp 100%

This study has enabled demonstrating the fact that only the emulsifiers of Examples 1 and 2 enable obtaining, under the experimental conditions mentioned, emulsions of the water-in-oil type when x is greater than or equal to 3% and y is greater than or equal to 20%, all the emulsifiers of Comparative Examples 1 to 6 leading to emulsions of the oil-in-water type.

The specificity of the emulsifiers based on oleyl glycoside and/or isostearyl glycoside is thus seen with respect to the alkyl glycosides of neighbouring chemical nature, with respect to the aptitude to forming water-in-oil emulsions.

A few examples of water-in-oil emulsions according to the invention will now be given in the cosmetic field of application.

EXAMPLES OF STABLE WATER-IN-OIL EMULSIONS ACCORDING TO THE INVENTION

These emulsions were prepared according to the following method:

a) a composition <<A>> (fatty phase) containing an emulsifier based on oleyl glycoside and/or isostearyl glycoside (product of Example 1 or of Example 2) is heated to 70°–75° C.;

b) a composition <<B>> (aqueous phase) is heated to 75° C.;

c) an emulsion is formed by mixing the aqueous phase <<B>> in the fatty phase <<A>> by means of a stirrer of the type SILVERSON 4'-4000 rpm d) cooling is effected under anchor stirrer;

e) a composition <C>> (preservative, perfume, colorants etc . . . ) was added around 40° C.

| W/O BABY CREAM | |
|---|---|
| A | |
| Product of Example 1 | 8% |
| Paraffin oil | 35% |
| Sweet almond oil | 5% |
| beeswax | 3% |
| castor oil | 2% |
| zinc oxide | 10% |
| SEPICALM ® VG | 1% |
| B | |

-continued

W/O BABY CREAM

| | |
|---|---|
| water | QSP 100 |
| glycerine | 5% |
| MgSO$_4$ | 0.7% |
| C | |
| Carotene | 0.05% |
| dl alpha tocopherol | 0.05% |
| perfume | 0.2% |
| SEPICIDE ® HB | 0.5% |
| SEPICIDE ® Cl | 0.2% |

W/O CREAM

| | |
|---|---|
| A | |
| Product of Example 2 | 5% |
| Squalane | 30% |
| MONTANE ® 481 | 2% |
| B | |
| water | QSP 100 |
| glycerine | 5% |
| SEPICALM ® S | 21% |
| C | |
| dl alpha tocopherol | 0.05% |
| perfume | 0.2% |
| SEPICIDE ® HB | 0.3% |
| SEPICIDE ® Cl | 0.2% |

VAPORISABLE W/O MOISTURISING MILK

| | |
|---|---|
| A | |
| Product of Example 1 | 8% |
| ELFACOS ST 9 | 2% |
| Mineral oil | 40% |
| SEPICIDE ® HB | 1% |
| B | |
| water | QSP 100 |
| glycerine | 5% |
| MgCl$_2$ | 0.7% |

W/O CREAM

| | |
|---|---|
| A | |
| Product of Example 1 | 3% |
| ELFACOS ® ST 9 | 2% |
| MONTANE ® 481 | 6% |
| Mineral oil | 30% |
| SEPICIDE ® HB | 1% |
| B | |
| water | QSP 100 |
| glycerine | 5% |
| MgCl$_2$ | 0.7%' |

What is claimed is:

1. Stable water-in-oil emulsion comprising:
   5 to 75% by weight of an aqueous phase;
   20 to 90% by weight of a fatty phase; and
   3 to 25% by weight of an emulsifier comprising:
      10 to 90% by weight, of a mixture of an oleyl glycoside having a degree of polymerisation of between 1 and 3 and an isostearyl glycoside having a degree of polymerisation of between 1 and 3; and
      90 to 10% by weight of a mixture of oleyl alcohol and isostearyl alcohol.

2. Water-in-oil emulsion comprising:
   5 to 75% by weight of an aqueous phase;
   20 to 90% by weight of a fatty phase; and
   3 to 25% by weight of an emulsifier comprising:
      10 to 50% by weight, of a mixture of an oleyl glycoside having a degree of polymerisation of between 1 and 3 and an isostearyl glycoside having a degree of polymerisation of between 1 and 3; and
      90 to 50% by weight of a mixture in any proportion of oleyl alcohol and isostearyl alcohol.

3. Stable water-in-oil emulsion comprising:
   5 to 75% by weight of an aqueous phase;
   20 to 90% by weight of a fatty phase; and
   3 to 25% by weight of an emulsifier comprising:
      10 to 40% by weight, of a mixture of an oleyl glycoside having a degree of polymerisation of between 1 and 3 and an isostearyl glycoside having a degree of polymerisation of between 1 and 3; and
      90 to 60% by weight of a mixture of oleyl alcohol and isostearyl alcohol.

4. The emulsion according to claim 1, wherein said emulsifier further comprises:
   up to 10% by weight of a co-emulsifier; and
   up to 10% by weight of a stabilizer.

5. The emulsion according to claim 2, wherein said emulsifier further comprises:
   up to 10% by weight of a co-emulsifier; and
   up to 10% by weight of a stabilizer.

6. The emulsion according to claim 3, wherein said emulsifier further comprises:
   up to 10% by weight of a co-emulsifier; and
   up to 10% by weight of a stabilizer.

7. The emulsion according to claim 1, which comprises:
   10 to 70% by weight of said aqueous phase;
   25 to 60% by weight of said fatty phase; and
   5 to 15% by weight of said emulsifier.

8. The emulsion according to claim 4, which comprises:
   10 to 70% by weight of said aqueous phase;
   25 to 60% by weight of said fatty phase; and
   5 to 15% by weight of said emulsifier.

9. The emulsion according to claim 1, wherein the emulsifier comprises:
   10 to 25% by weight of an isostearyl glycoside having a degree of polymerisation of between 1 and 3; and
   90 to 75% by weight of an isostearyl alcohol.

10. The emulsions according to claim 4, wherein the emulsifier comprises:
    10 to 25% by weight of an isostearyl glycoside having a degree of polymerisation of between 1 and 3; and
    90 to 75% by weight of an isostearyl alcohol.

11. The emulsion according to claim 1, wherein the emulsifier comprises:
    10 to 25% by weight of an oleyl glycoside having a degree of polymerisation of between 1 and 3; and
    90 to 75% by weight of an oleyl alcohol.

12. The emulsion according to claim 4, wherein the emulsifier mentioned above comprises:

10 to 25% by weight of an oleyl glycoside having a degree of polymerisation of between 1 and 3; and 90 to 75% by weight of an oleyl alcohol.

13. The emulsion according to claim 1, which comprises:

30 to 40% by weight of said fatty phase; and 3 to 10% by weight of said emulsifier comprising:
10 to 25% by weight of an isostearyl glycoside having a degree of polymerisation of between 1 and 3; and
90 to 75% by weight of isostearyl alcohol.

14. The emulsion according to claim 4, which comprises:

30 to 40% by weight of said fatty phase; and 3 to 10% by weight of said emulsifier comprising:
10 to 25% by weight of an isostearyl glycoside having a degree of polymerisation of between 1 and 3; and
90 to 75% by weight of isostearyl alcohol.

15. The emulsion according to claim 1, which comprises:

30 to 40% by weight of said fatty phase; and 3 to 10% by weight of said emulsifier comprising:
10 to 25% by weight of an isostearyl glycoside having a degree of polymerisation of between 1 and 3;
90 to 75% by weight of isostearyl alcohol;
up to 6% by weight of a co-emulsifier; and
up to 2% by weight of a stabilizer.

16. The emulsion according to claim 1, wherein the fatty phase comprises at least one mineral oil.

17. The emulsion according to claim 4, wherein the co-emulsifier is comprises a sorbitan ester.

18. The emulsion according to claim 4, wherein the stabilizer above is selected from the group consisting of polyethylene glycol—dodecyl glycol copolymers, beeswax, stearic acid and hydrogenated castor oil.

19. The emulsion according to claim 4, which comprises, as co-emulsifier and stabilizer, a mixture of beeswax, hydrogenated castor oil, stearic acid and sorbitan oleate.

20. A method for preparing a stable water-in-oil emulsion, comprising 5 to 75% by weight of an aqueous phase, 20 to 90% by weight of a fatty phase and 3 to 25% by weight of an emulsifier, said method comprising using as emulsifier:

10 to 90% by weight, of a mixture of an oleyl glycoside having a degree of polymerisation of between 1 and 3 and an isostearyl glycoside having a degree of polymerisation of between 1 and 3; and 90 to 10% by weight of a mixture of oleyl alcohol and isostearyl alcohol.

21. The method according to claim 20, wherein said emulsifier further comprises:

up to 10% by weight of a co-emulsifier; and up to 10% by weight of a stabilizer.

22. The method according to claim 20, wherein the emulsion comprises:

10 to 70% by weight of an aqueous phase;

25 to 60% by weight of a fatty phase; and 5 to 15% by weight of said emulsifier.

23. The method according to claim 20, wherein the emulsifier comprises:

10 to 25% by weight of an isostearyl glycoside having a degree of polymerisation of between 1 and 3; and 90 to 75% by weight of an isostearyl alcohol.

24. The method according to claim 20, wherein the emulsifier comprises:

10 to 25% by weight of an oleyl glycoside having a degree of polymerisation of between 1 and 3; and 90 to 75% by weight of an oleyl alcohol.

25. The method according to claim 21, wherein the emulsifier comprises:

10 to 25% by weight of an oleyl glycoside having a degree of polymerisation of between 1 and 3; and 90 to 75% by weight of an oleyl alcohol.

26. The method according to claim 20, wherein the emulsion comprises:

30 to 40% by weight of a fatty phase; and 3 to 10% by weight of an emulsifier comprising:
10 to 25% by weight of an isostearyl glycoside having a degree of polymerisation of between 1 and 3; and
90 to 75% by weight of isostearyl alcohol.

27. The method according to claim 21, wherein the emulsion comprises:

30 to 40% by weight of said fatty phase; and 3 to 10% by weight of said emulsifier comprising:
10 to 25% by weight of an isostearyl glycoside having a degree of polymerisation of between 1 and 3; and
90 to 75% by weight of isostearyl alcohol.

28. The method according to claim 20, wherein the emulsion comprises:

30 to 40% by weight of said fatty phase; and 3 to 10% by weight of said emulsifier comprising:
10 to 25% by weight of an isostearyl glycoside having a degree of polymerisation of between 1 and 3; and
90 to 75% by weight of isostearyl alcohol;
up to 6% by weight of a co-emulsifier; and
up to 2% by weight of a stabiliser.

29. The method according to claim 20, wherein the fatty phase comprises at least one mineral oil.

30. The method according to claim 21, wherein the co-emulsifier comprises a sorbitan ester.

31. The method according to claim 21, wherein the stabilizer is selected from the group consisting of polyethylene glycol—dodecyl glycol copolymers, beeswax, stearic acid and hydrogenated castor oil.

32. The method according to claim 21, wherein the emulsion comprises, as co-emulsifier and stabilizer, a mixture of beeswax, hydrogenated castor oil, stearic acid and sorbitan oleate.

* * * * *